(12) United States Patent
Haran

(10) Patent No.: US 7,968,860 B2
(45) Date of Patent: Jun. 28, 2011

(54) SYSTEM AND METHOD FOR MEASUREMENT OF DEGREE OF MOISTURE STRATIFICATION IN A PAPER OR BOARD

(75) Inventor: Frank M Haran, North Vancouver (CA)

(73) Assignee: Honeywell International Inc, Morristown, NJ (US)

( * ) Notice: Subject to any disclaimer, the term of this patent is extended or adjusted under 35 U.S.C. 154(b) by 0 days.

(21) Appl. No.: 11/881,321

(22) Filed: Jul. 26, 2007

(65) Prior Publication Data
US 2009/0027655 A1    Jan. 29, 2009

(51) Int. Cl.
*G01N 15/06* (2006.01)
*G01N 21/86* (2006.01)
*G01J 5/02* (2006.01)

(52) U.S. Cl. .................. 250/575; 250/339.1; 250/559.11

(58) Field of Classification Search .................. 250/574, 250/575, 339.1, 559.11; 356/238.2; 324/637, 324/639, 640, 642, 643
See application file for complete search history.

(56) References Cited

U.S. PATENT DOCUMENTS

| | | | | |
|---|---|---|---|---|
| 4,019,819 A | * | 4/1977 | Lodzinski | 356/73 |
| 4,789,820 A | * | 12/1988 | Parrent et al. | 324/640 |
| 5,049,216 A | | 9/1991 | Shead et al. | |
| 5,086,279 A | * | 2/1992 | Wochnowski et al. | 324/637 |
| 5,124,552 A | | 6/1992 | Anderson | |
| 5,235,192 A | | 8/1993 | Chase et al. | |
| 7,034,324 B2 | * | 4/2006 | Voser | 250/556 |
| 2004/0223147 A1 | * | 11/2004 | Fujimoto et al. | 356/239.1 |
| 2006/0132796 A1 | * | 6/2006 | Haran | 356/503 |
| 2006/0243931 A1 | | 11/2006 | Haran et al. | |
| 2007/0295077 A1 | * | 12/2007 | Hellstrom | 73/159 |

FOREIGN PATENT DOCUMENTS

| | | |
|---|---|---|
| EP | 0257849 A2 | 3/1988 |
| WO | WO 2006/118619 | 11/2006 |

* cited by examiner

*Primary Examiner* — Thanh X Luu

(57) ABSTRACT

A measurement system for measuring a degree of moisture stratification in a flat sheet product, such as paper, board or other materials. The system uses a combination of a reflection gauge and a transmission gauge to provide output signals indicative of surface moisture of a first side and of moisture in the body of the flat sheet product. The output signals are processed by a controller or computer to provide a measurement of the moisture stratification. An additional reflection gauge and an additional transmission gauge can also be used to provide additional output signals indicative of surface moisture of a second side of the flat sheet product and of moisture in the body. Narrow band radiation is used with modulation to distinguish from ambient radiation as well as radiation incident on the opposite side.

25 Claims, 4 Drawing Sheets

SYSTEM AND METHOD FOR MEASUREMENT OF DEGREE OF MOISTURE STRATIFICATION IN A PAPER OR BOARD

FIELD OF THE INVENTION

This invention relates to a system and method for measuring the degree of moisture stratification in a flat sheet product, such as paper or board products.

BACKGROUND OF THE INVENTION

It is often necessary during manufacture to measure the water content of flat sheet products, such as paper or board products. Currently available measurement systems attempt to measure the total amount of moisture (i.e. water), contained in the flat sheet product with no indication of where the moisture is located within the depth or bulk of the sheet. However, it is advantageous to know where the moisture is within the depth of many paper or board products. Problems, such as curl, can occur if the moisture does not have the proper depth profile in the product. Curl can later lead to a reduction in the manufacturing speeds of processes that use the paper or board product, e.g. when making such things as boxes and containers.

There is a need for a system and method that provides a measurement of the location of moisture within the depth of a flat sheet product.

SUMMARY OF THE INVENTION

The measurement system of the present invention measures a degree of stratification of moisture in a moving flat sheet product. The measurement system comprises at least a first reflection gauge that is located at a measurement station adjacent the moving flat sheet product and that provides a reflection output signal. At least a first transmission gauge is located at the measurement station and provides a transmissive output signal. A controller processes the reflection output signal and the transmissive output signal to provide a measurement of a degree of stratification of moisture in the flat sheet product.

In another embodiment of the measurement system of the present invention, a second reflection gauge is located at the measurement station and provides a reflection output signal. A second transmission gauge is located at the measurement station and provides a transmissive output signal. The controller processes the reflection output signals of the first and second reflection gauges and the transmissive output signals of the first and second transmission gauges to provide the measurement.

In another embodiment of the measurement system of the present invention, one or more sources provide radiation incident to first and second sides of the flat sheet product at the measurement station. The reflection output signals of the first and second reflection gauges are derived from a reflection of the radiation incident to the first and second sides, respectively. The transmissive output signals of the first and second transmission gauges are derived from the radiation that emerges from the second and first sides, respectively.

In another embodiment of the measurement system of the present invention, the radiation incident on the first and second sides of the flat sheet product is differentiated to eliminate cross talk.

In another embodiment of the measurement system of the present invention, the radiation incident on the first and second sides of the flat sheet product is modulated at different frequencies. The reflection output signals of the first and second reflection gauges and the transmissive output signals of the first and second transmission gauges are demodulated.

In another embodiment of the measurement system of the present invention, the radiation comprises at least first and second bandwidths, wherein the modulation frequencies comprise first and second frequencies for the first and second bandwidths of the radiation incident on the first side, respectively, and third and fourth frequencies for the first and second bandwidths of the radiation incident on the second side, respectively.

In another embodiment of the measurement system of the present invention, one or more demodulators demodulate the reflection signals of the first and second reflection gauges and the transmissive signals of the first and second transmissive gauges. The controller processes the demodulated reflection output signals of the first and second reflection gauges and the demodulated transmissive output signals of the first and second transmission gauges to provide the measurement.

In another embodiment of the measurement system of the present invention, at least one source of radiation provides radiation to a first side of the flat sheet product. The reflection gauge comprises a receiver that receives a reflection of the radiation from the first side to provide the reflection output signal. The transmission gauge comprises a receiver that receives a portion of the radiation that passes through the flat sheet product and emerges from a second side thereof to provide the transmissive output signal.

In another embodiment of the measurement system of the present invention, a first optical head comprises a transmitter that directs the radiation to the first side of the flat sheet product and to the receiver of the reflection gauge. A second optical head comprises the receiver of the transmission gauge.

In another embodiment of the measurement system of the present invention, the reflection gauge and the transmission gauge comprise an implementation selected from the group consisting of: scanning a cross direction of the flat sheet product and stationary in a machine direction of the flat sheet product.

In another embodiment of the measurement system of the present invention, the radiation is in a wavelength band about a wavelength selected from the group consisting of: 1.3, 1.44, 1.8 and 1.94 microns.

In another embodiment of the measurement system of the present invention, the radiation comprises a first wavelength band and a second wavelength band that are modulated at a first frequency and a second frequency, respectively. First and second demodulators that are tuned to the first and second frequencies demodulate the reflection output signal and the transmissive output signal. The controller processes the demodulated reflection output signal and the demodulated transmissive output signal to provide the measurement.

The method of the present invention measures a degree of stratification of moisture in a moving flat sheet product by performing the steps comprising:

providing a first output signal derived from a reflection of radiation incident on a first side of the moving flat sheet product;

providing a second output signal derived from an emergence of the radiation from a second side of the flat sheet product; and processing the first and second output signals to provide a measurement of a degree of stratification of moisture in the flat sheet product.

In another embodiment of the method of the present invention, the step of providing a first output signal uses a reflection gauge and the step of providing a second output signal uses a transmission gauge.

In another embodiment of the method of the present invention, the radiation is in a wavelength band about a wavelength selected from the group consisting of: 1.3, 1.44, 1.8 and 1.94 microns.

In another embodiment of the method of the present invention, the radiation comprises a first wavelength band and a second wavelength band that are modulated at a first frequency and a second frequency, respectively. The method also comprises demodulating the first and second output signals, which are processed to provide the measurement.

In another embodiment of the method of the present invention, the method performs the further steps comprising:
  providing a third output signal derived from a reflection of radiation incident on a second side of the moving flat sheet product;
  providing a fourth output signal derived from an emergence of the radiation, which is incident on the second side of the flat sheet product, from the first side of the flat sheet product; and wherein the processing step also processes the third and fourth output signals to provide the measurement of a degree of stratification of moisture in the flat sheet product.

In another embodiment of the method of the present invention, the method comprises the step of differentiating the radiation incident on the first and second sides of the flat sheet product to eliminate cross talk.

In another embodiment of the method of the present invention, the step of differentiating comprises modulating the radiation incident on the first and second sides at different frequencies, and demodulating the first, second, third and fourth output signals.

BRIEF DESCRIPTION OF THE DRAWINGS

Other and further objects, advantages and features of the present invention will be understood by reference to the following specification in conjunction with the accompanying drawings, in which like reference characters denote like elements of structure and.

DESCRIPTION OF THE PREFERRED EMBODIMENT

The measurement system of the present invention combines a transmission moisture gauge with a reflection moisture gauge to measure the degree of stratification (DOS) within a sample flat sheet product. For the preferred embodiment described herein, the moisture is water in a cellulose-based material, such as paper or board. In other embodiments, the moisture could be a different liquid. A reflection moisture gauge predominately measures the surface water in the flat sheet product. The majority of the reflection moisture gauge's output signal comes from the first 100 or 200 microns of the surface of the flat sheet product. On the other hand, a transmission moisture gauge measures the average moisture in the flat sheet product. The measurement output signals of these two gauges can be used to indicate the moisture content in the top (the side on which the moisture gauge is located) and the remainder of the flat sheet product. If a reflection moisture gauge is used on either side of the flat sheet product in combination with a transmission gauge, it is possible to get an indication of the relative moisture contained on both sides of the flat sheet product as well as the average moisture of the total flat sheet product. The reflection moisture gauge/s preferably uses light in the infrared (IR) region of the spectrum. For commonality of components, the transmission moisture gauge also can use IR transmission, but alternatively could use transmission in other regions (e.g., microwave or Terahertz) of the spectrum.

Figure 1:
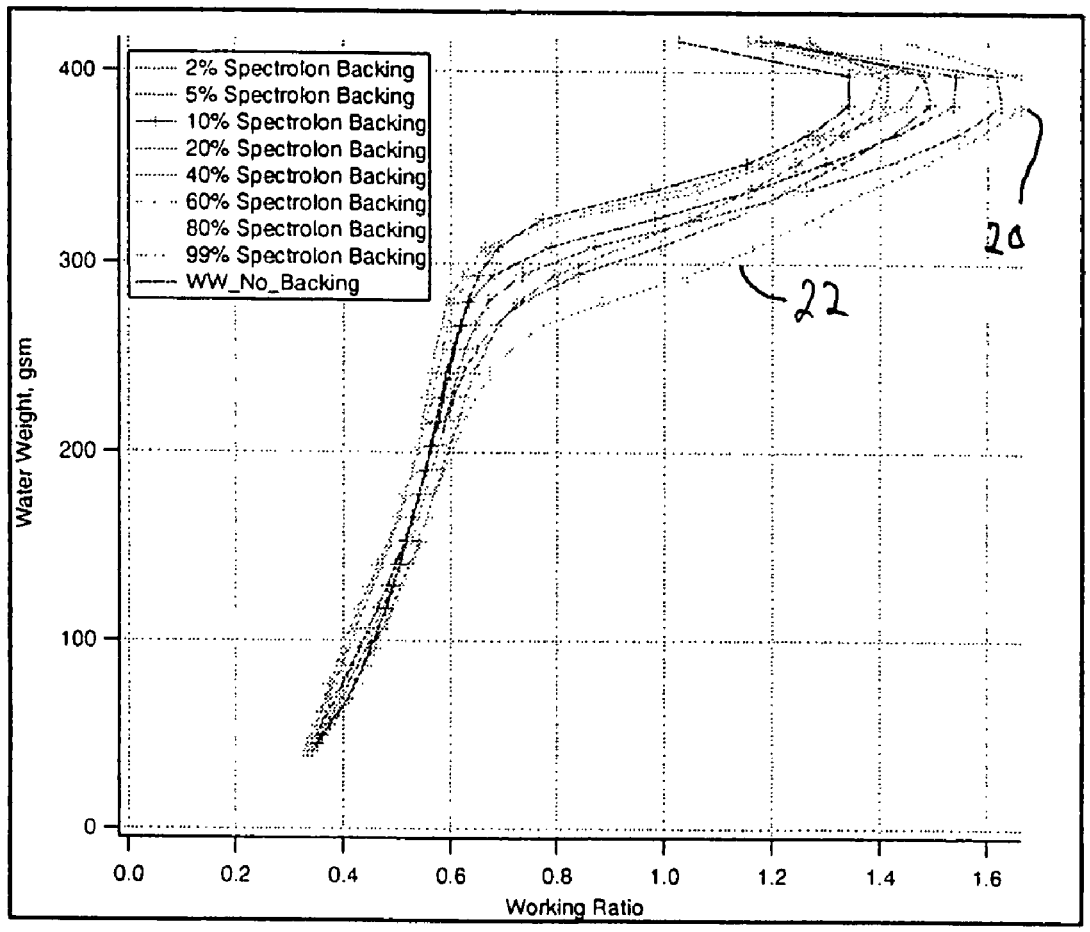
FIG. 1 is a graph that depicts a set dry down calibration curves for a board sample.

Referring to FIG. 1, a plurality of dry down calibration curves for board samples of different backings is shown. A dry down calibration is the process for wetting a sample up to a certain level of moisture content (usually saturation). The sample is then placed on a gravimetric scale, which measures the amount of water in the sample. The amount of water in the sample decreases over time due to evaporation and the scale is read by a computer so that the reduction in water over time can be traced. Simultaneously, an IR moisture gauge reads the sample and the computer that is reading the scale records the response from the IR moisture gauge. From the independent scale measurement the IR moisture gauge is calibrated. With the knowledge of the size of the sample on the scale and the bone dry weight of the sample it is a simple matter to calculate the moisture content of the sample. Weights are measured in grams per square meter (gsm). The backings range from no backing to 99% (light reflection) backing (for example, a lambertian diffuse scatterer). The knees in these curves are due to more water being present in the middle or the bottom of the samples than is present on the top surface. Sometimes this concentration can be higher on the top than in the middle. Other times it can be concentrated in the middle or the bottom. The sensor gives an indication of these concentrations.

In a preferred embodiment, the measurement system employs frequency modulation of the amplitude of each optical source used in the optical heads similar to the method described in International Publication No. WO2006/118619, which is incorporated herein by reference in its entirety. Radiation sources, such as light emitting diodes (LEDs) or laser devices, are operated in wavelength bands of interest and are each uniquely amplitude modulated at various frequencies. The modulated light is delivered by optical fiber to an optical head that in turn delivers the modulated light to the flat sheet product. In preferred embodiments of the present invention, first and second optical heads are disposed in optical alignment on opposite sides of the flat sheet product so that a reflection gauge and a transmission gauge are deployed on each side. The optical heads receive the modulated reflected light and the modulated transmissive light from the surface of the flat sheet product, which is coupled to detectors for demodulation and processing. These two heads on opposite side of the sheet operate both as transmission gauges and reflection gauges.

Figure 2:
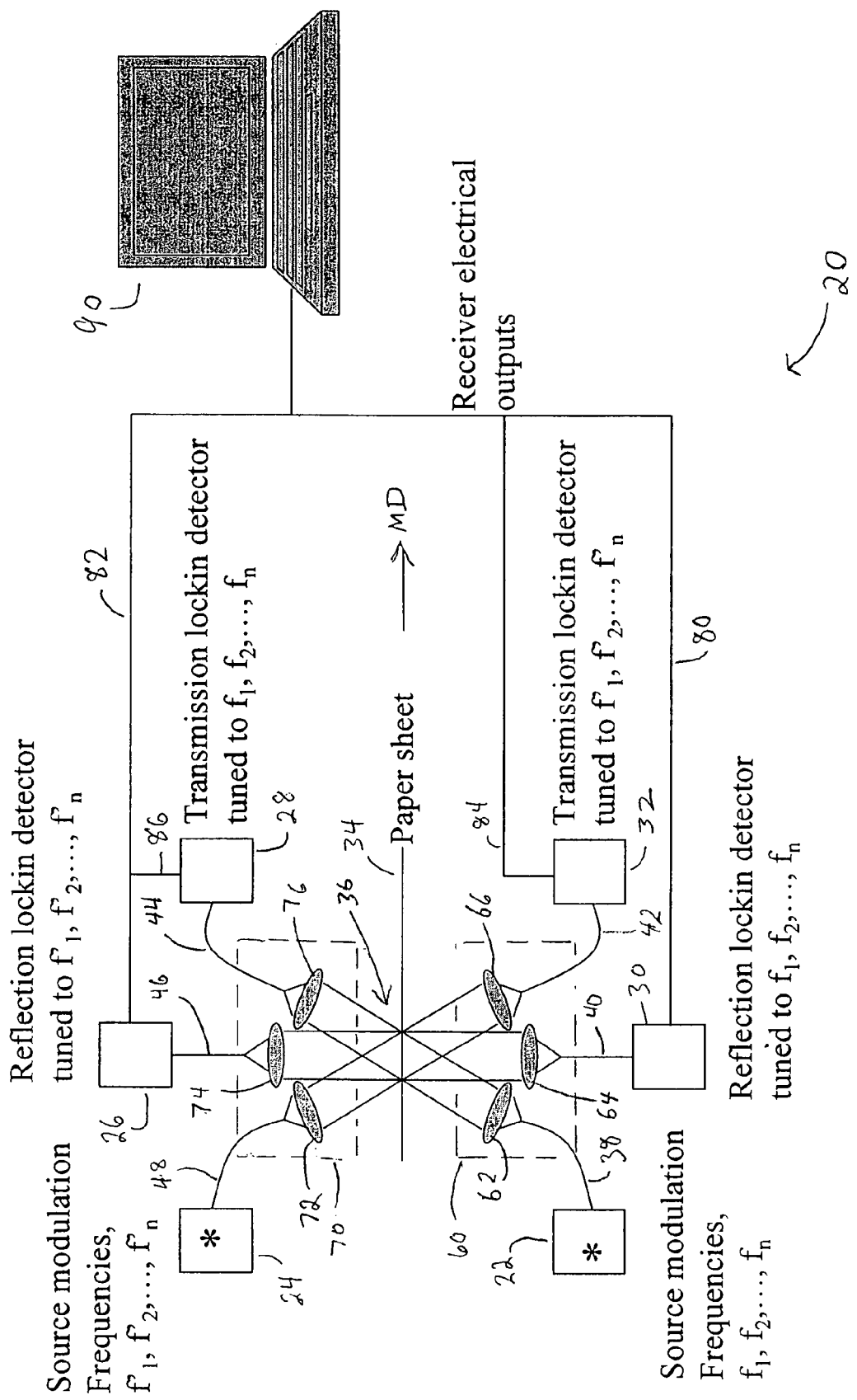
FIG. 2 is a is a block diagram of a measurement system of the present invention.

Referring to FIG. 2, a measurement system 20 of the present invention measures the moisture content of a flat sheet product 34 that is conveyed past a measurement station 36 in a machine direction MD to a take up spool (not shown).

Measurement system 20 comprises a radiation source 22, a radiation source 24, an optical head 60, an optical head 70, a reflection lockin detector 26, a transmission lockin detector 28, a reflection lockin detector 30, a transmission lockin detector 32 and a controller 90.

Radiation source 22 provides radiation in a wavelength band about a wavelength of 1.3 microns (reference) and/or 1.44 microns (measurement). The reference source is modulated at $f_1$ and the measurement source is modulated at $f_2$. If more than two wavelengths are used, then the other wavelength source(s) are modulated at $f_n$ where n is an integer equal to the number of sources (wavelength bands) used. Other wavelengths may be used for temperature or cellulose correctors. Radiation source 24 provides radiation in the same wavelength band, which is modulated at different (e.g., lower) frequencies of $f_1'$, $f_2'$, ... $f_n'$. The radiation source 24 provides radiation at the same wavelengths as those provided by radiation source 22, but are modulated with different frequencies in order to differentiate them from radiation provided by radiation source 22 and chosen to eliminate cross talk between channels. Therefore, if radiation source 24 provides a reference and measure radiation at wavelengths of 1.3 microns and 1.44 microns respectively, then they would be modulated at frequencies $f'_1$ and $f'_2$ respectively. Frequencies $f_1$, $f_2$, $f'_1$, and $f'_2$ are different from each other and are chosen to minimize cross talk between the channels. The frequencies are single frequency and typically in the range of 10 kHz to 100 MHz.

The radiation outputs of radiation sources 22 and 24 are conveyed by optical connectors 38 and 48 to optical heads 60 and 70, respectively. Optical heads 60 and 70 are disposed on opposite sides of flat sheet product 34. Thus, optical head 60 is disposed below and optical head 70 is disposed above flat sheet product 34 in FIG. 2.

Each of the optical heads 60 and 70 comprise an optical transmitter and two optical receivers. Optical head 60 comprises an optical transmitter 62 that directs the radiation received via optical connector 38 to the lower surface of flat sheet product 34 at measurement station 32. Optical head 70 comprises optical transmitter 72 that directs the radiation received via optical connector 48 to the upper surface of flat sheet product 34 at measurement station 32.

Optical head 60 further comprises an optical receiver 64 that is positioned to receive the radiation of radiation source 22 reflected from the lower surface of flat sheet product 34. Optical head 70 further comprises an optical receiver 74 that is positioned to receive the radiation of radiation source 24 reflected from the upper surface of flat sheet product 34.

Optical head 60 further comprises an optical receiver 66 that is positioned to receive the radiation of radiation source 24 transmitted through flat sheet product 34. Optical head 70 further comprises an optical receiver 76 that is positioned to receive the radiation of radiation source 22 transmitted through flat sheet product 34.

In alternate embodiments, optic receiver 74 and 76 may be combined, fibers 46 and 44 may be combined, and/or lockin detector 26 and 28 may be combined. Similar combinations can also be done with optical head 60.

The reflected radiation from optical receiver 64 is coupled by an optical connector 40 to reflection lockin detectors 30, which are tuned to frequencies $f_1$, $f_2$, ... $f_n$ for demodulation and conversion to an electrical signals that is coupled via an electrical connections 80 to controller 90. The reflected radiation from optical receiver 74 is coupled by an optical connector 46 to reflection lockin detectors 26, which are tuned to frequencies $f_1'$, $f_2'$, ... $f_n'$ for demodulation and conversion to an electrical signals that is coupled via an electrical connections 82 to controller 90.

The transmissive radiation from optical receiver 66 is coupled by an optical connector 42 to transmission lockin detectors 32, which are tuned to frequencies $f_1'$, $f_2'$, ... $f_n'$ for demodulation and conversion to an electrical signals that is coupled via an electrical connections 84 to controller 90. The transmissive radiation from optical receiver 76 is coupled by an optical connector 44 to transmissive lockin detectors 28, which are tuned to frequencies $f_1$, $f_2$, ... $f_n$ for demodulation and conversion to an electrical signals that is coupled via an electrical connections 86 to controller 90.

Radiation sources 22 and 24 contain LEDs or laser devices that provide radiation in the wavelength bands of interest, such as those described in WO 2006/118619. For example, radiation sources 22 and 24 are preferably combination light source and modulation units that are directly modulated via a drive current at high frequencies. The wavelengths for water are about 1.3 microns for the reference reading and about 1.44 microns for the measurement reading. The modulation single frequencies typically in the range 10 kHz to 100 MHz.

Optical connectors 38, 40, 42, 44, 46 and 48 are preferably optical fibers. Optical transmitters 62 and 72 are preferably mirrors (off-axis paraboloids) or lens. Optical receivers 64, 66, 74 and 76 are preferably mirrors (off-axis paraboloids) or lens.

Optical transmitters 62 and 72 direct the radiation at an angle θ to the surface normal of flat sheet product 34. The reflected radiation is captured by optical receivers 64 and 74 at an angle of about 90° to surface of flat sheet product 34. A typical value for θ is about 30° to avoid any specularly reflected component from the surface of flat product sheet 34. However, in a lot of cases where no specular surface reflection is present smaller angles can be used. Also note that many other angles can be used.

Controller 90 is preferably a computer (e.g., a personal computer or a work station) that comprises a memory, a processor, and one or more input/output devices, such as a display, a printer, a keyboard, a mouse and the like. Controller 90 preferably comprises a program that transforms the measurement readings into a form that is useful to an operator. For example, the program derives from the readings dry down calibration curves similar to those shown in FIG. 1.

In measurement system 20, optical heads 60 and 70 can be deployed to measure moisture along the cross direction, the machine direction MD or both directions of a paper or board making machine. Optical heads 60 and 70 can be scanned across the moving flat sheet product. For measuring moisture in the machine direction MD, it is preferred that a plurality of the optical heads 60 and 70 be deployed essentially in tandem at different MD locations, but at the same cross direction location relative to the edges of flat sheet product 34.

In alternative embodiments, measurement system 20 uses a grating based spectrometer to produce a set of absorption characteristics that are supplied to a controller that deduces from the absorption characteristics the degree of moisture stratification at the location of flat sheet product 34 that was measured.

In another alternative embodiment, measurement system 20 can use quartz tungsten halogen lamps with mechanical choppers as the source and photodetectors with interference filters as the receivers.

Figure 3:
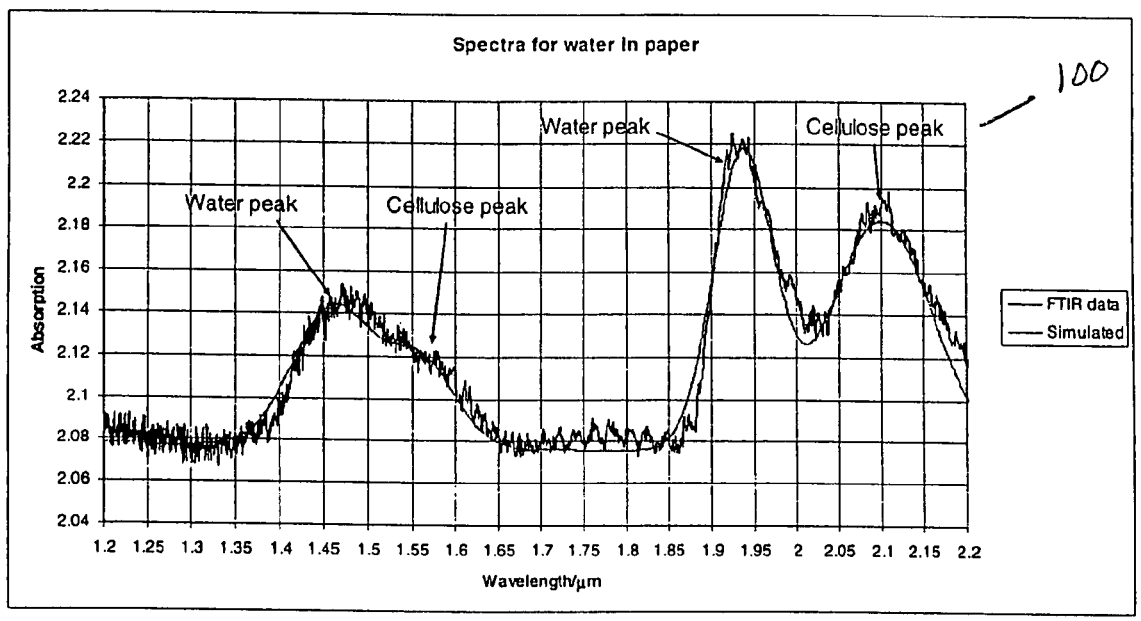
FIG. 3 depicts the absorption spectra of liquid water contained within a paper substrate.

Referring to FIG. 3, a graph 100 shows spectra for water in paper in which absorption is the ordinate and wavelength in microns (micrometers) is the abscissa. The data for graph 100 was taken using a FTIR (Fourier Transform Infrared) spectrometer. Water content peaks occur at approximately 1.44 and 1.94 microns. At these wavelengths (the water content peaks), radiation has a higher absorption than radiation at other wavelengths. That is, the depth of radiation penetration into the flat sheet sample is dependent on the wavelength of the radiation. For example, radiation at a wavelength of 1.45 microns penetrates less than radiation at a wavelength of 1.40 wavelength.

Traditional paper moisture gauges obtain the moisture content in the relative absorption in two or three wavelength bands. In a two-wavelength band gauge, an absorption measurement is made in a reference band and in a measurement band. The measurement band might be at 1.94 microns peak with a FWHM (Full Width Half Maximum) of 50 nanometers (contains a water absorption peak) and the reference band might be at 1.80 microns with a FWHM (Full Width Half Maximum) of 50 nanometers (minimal water content) in graph 100. The reference band is preferably chosen to be near the measurement band because it provides the best referencing for non-moisture related signal variations. Sometimes a third wavelength band is also used which contains a cellulose peak, such as 2.1 microns in graph 100.

Figure 4:
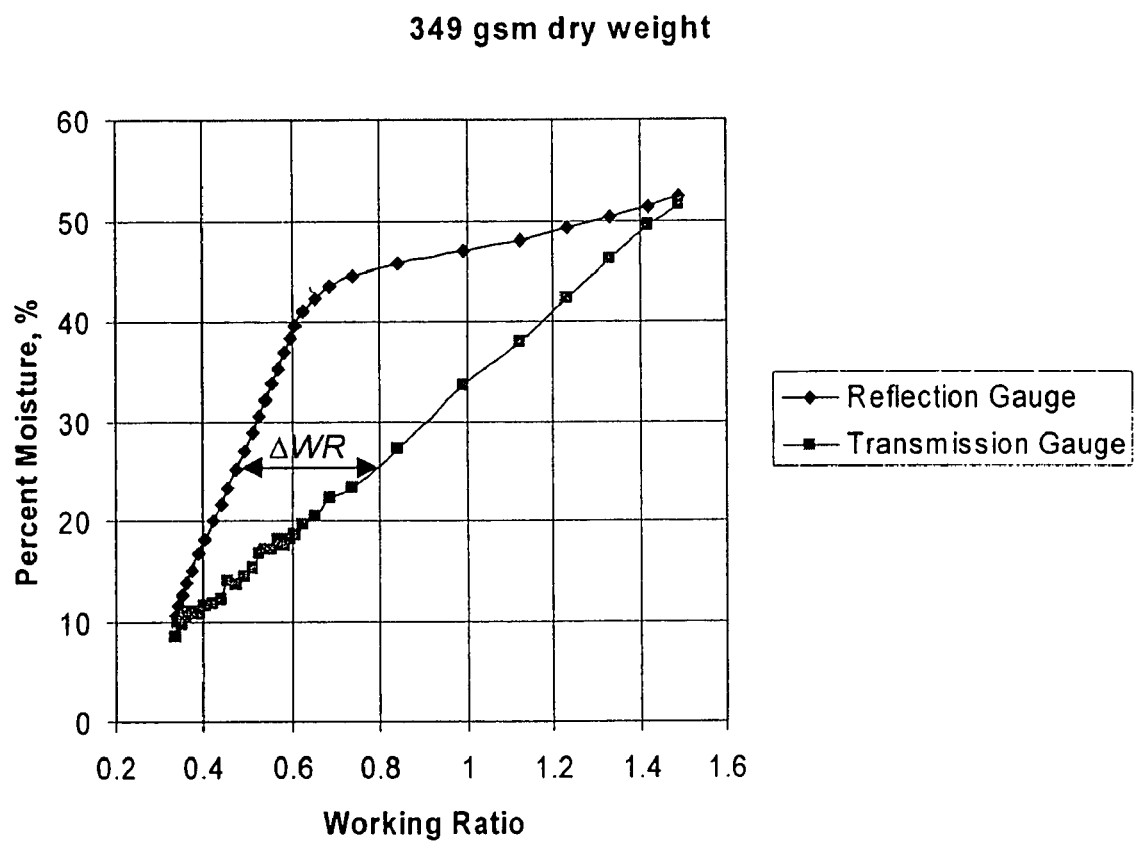
FIG. 4 is a graph that depicts typical outputs of a transmission gauge and a reflection gauge used in the measurement of moisture in a flat sheet product with moisture stratification present.

Referring to FIG. 4, a typical output from a transmission moisture gauge and a reflection moisture gauge is graphically depicted. The ordinate is percentage of moisture and the abscissa is the working ratio (WR). The WR reading from a transmission gauge is unaffected by moisture stratification whereas the WR reading from a reflection gauge is dependent upon the moisture stratification in the flat sheet product. As the moisture stratification becomes more severe in the flat sheet product, then the size of the hump in the reflection gauges transfer characteristic moves further left and $\Delta$WR get larger, hence the degree of moisture stratification, $\Pi$, can be expressed as a function of $\Delta$WR:

$$\Pi = f(\Delta WR), \quad (1)$$

where $\Delta WR = WR_{transmission} - WR_{reflection}$ and $WR_{transmission}$ and $WR_{reflection}$ are the working ratios of the transmission gauge and reflection gauge respectively. The working ratio, WR is given by:

$$WR = \frac{CR_m}{CR_r} - 1, \quad (2)$$

where $CR_m$ and $CR_r$ are known as the measure and reference channel ratios respectively. The channel ratios are given by:

$$CR_k = \frac{SV_k - DV_k}{CV_k - DV_k}, \quad (3)$$

where the subscript k has the value of m or r, which represent reference and measure channels respectively and SV, DV and CV are the standardization, dark and channel voltages respectively.

One possible measure of degree of moisture stratification can be defined as:

$$\Pi = \frac{PM_{bulk} - PM_{surface}}{\overline{PM}}, \quad (4)$$

where $PM_{bulk}$ is the percentage moisture of the bulk (excludes the moisture in surface on the source side), $PM_{surface}$, is the percent moisture on the source side surface and $\overline{PM}$ is the average percent moisture of the entire sheet. We are generally interested in the two-sidedness of the product and we therefore measure the $\Pi$ of the top and bottom surface, i.e. $\Pi_{top}$, and $\Pi_{bottom}$. The functional form of equation (1) is obtained via calibration, which can be obtained either on or off machine. The program in controller 90 can include a procedure that uses equations (1)-(4) to provide degree of stratification data to a user by a display or a printer.

The present invention having been thus described with particular reference to the preferred forms thereof, it will be obvious that various changes and modifications may be made therein without departing from the spirit and scope of the present invention as defined in the appended claims.

What is claimed is:

1. A measurement system for measuring a degree of stratification of moisture in a moving flat sheet product, said system comprising:
    one or more sources that provide radiation incident to first and second sides of said moving flat sheet product at a measurement station adjacent said moving flat sheet product;
    a first reflection gauge and a second reflection gauge that are located on said first and second sides of said moving flat sheet product at said measurement station and that respond to said radiation in the infrared range to provide first and second reflection output signals, respectively;
    a first transmission gauge and a second transmission gauge that are located on said first and second sides of said moving flat sheet product at said measurement station and that provide first and second transmissive output signals, respectively; and
    a controller that processes said first and second reflection output signals and said first and second transmissive output signals to provide a measurement of a degree of stratification of moisture within said moving flat sheet product, and wherein said measurement comprises a moisture value of a location within a depth of said moving flat sheet product.

2. The measurement system of claim 1, wherein said one or more sources comprise a first source and a second source that provide radiation incident to first and second sides of said moving flat sheet product at said measurement station, respectively, wherein said first and second reflection output signals are derived from a reflection of infrared radiation incident to said first and second sides, respectively, and wherein first and second transmissive output signals are derived from the radiation that emerges from said second and first sides, respectively.

3. The measurement system of claim 2, wherein the radiation incident on the first and second sides of said moving flat sheet product is differentiated to eliminate cross talk.

4. The measurement system of claim 3, wherein the radiation incident on said first and second sides of said moving flat sheet product is modulated at different frequencies, and wherein said first and second reflection output signals of the first and second reflection gauges and said first and second transmissive output signals of the first and second transmission gauges are demodulated.

5. The measurement system of claim 4, wherein said radiation comprises at least first and second bandwidths, wherein said modulation frequencies comprise first and second frequencies for the first and second bandwidths of the radiation incident on said first side, respectively, and third and fourth frequencies for the first and second bandwidths of the radiation incident on said second side, respectively.

6. The measurement system of claim 5, further comprising one or more demodulators that demodulate said first and second reflection signals of said first and second reflection gauges and said first and second transmissive signals of said first and second transmissive gauges, and wherein said controller processes said first and second demodulated reflection output signals and said first and second demodulated transmissive output signals to provide said measurement.

7. The measurement system of claim 2, wherein said first reflection gauge comprises a first reflection receiver that receives a reflection of said radiation from said first side to provide said first reflection output signal, and wherein said first transmission gauge comprises a first transmissive receiver that receives a portion of said radiation that passes through said moving flat sheet product and emerges from said second side thereof to provide said first transmissive output signal.

8. The measurement system of claim 7, further comprising a first optical head that comprises a transmitter that directs said radiation provided by said first source to said first side of said moving flat sheet product and said first reflection receiver and a second optical head that comprises said first transmissive receiver of said first transmission gauge.

9. The measurement system of claim 2, wherein said radiation provided by said first source comprises a first wavelength band and a second wavelength band that are modulated at a first frequency and a second frequency, respectively, wherein said radiation provided by said second source comprises said first wavelength band and said second wavelength band that are modulated at a third frequency and a fourth frequency, respectively, and further comprising first, second, third and fourth demodulators that are tuned to said first, second, third and fourth frequencies to demodulate said first reflection output signal, said first transmissive output signal, said second reflection output signal and said second transmissive signal, respectively, and wherein said controller processes said demodulated first reflection output signal, said first demodulated first transmissive output signal, said demodulated second reflection output signal and said demodulated second transmissive signal to provide said measurement.

10. The measurement system of claim 1, wherein said first and second reflection gauges and said first and second transmission gauges comprise an implementation selected from the group consisting of: scanning a cross direction of said flat sheet product and stationary in a machine direction of said moving flat sheet product.

11. The measurement system of claim 2, wherein said radiation is in a wavelength band about a wavelength selected from the group consisting of: 1.3, 1.44, 1.8 and 1.94 microns.

12. The measurement system of claim 1, wherein said first and second transmission gauges respond to radiation in a range selected from the group consisting of: infrared and microwave.

13. The measurement system of claim 1, wherein said controller derives from said measurement of degree of stratification of moisture a dry down calibration curve for said flat sheet product.

14. A method for measuring a degree of stratification of moisture in a moving flat sheet product, said method comprising:
providing radiation incident on first and second sides of said moving flat sheet product;
providing a first reflection output signal and a second reflection output signal derived from a reflection of said radiation incident on said first and second sides of said moving flat sheet product, wherein said first and second reflection is of said radiation in the infrared range;
providing a first transmissive output signal and a second transmissive output signal derived from an emergence of said radiation from said second and first sides of said moving flat sheet product, respectively; and
processing said first and second reflection output signals and said first and second transmissive output signals to provide a measurement of a degree of stratification of moisture within said moving flat sheet product, and wherein said measurement comprises a moisture value of a location within a depth of said moving flat sheet product.

15. The method of claim 14, wherein said first and second reflection output signals are provided by first and second reflection gauges, respectively, and wherein said first and second transmissive output signals are provided by first and second transmission gauges, respectively.

16. The method of claim 14, wherein said radiation is in a wavelength band about a wavelength selected from the group consisting of: 1.3, 1.44, 1.8 and 1.94 microns.

17. The method of claim 14, wherein said radiation comprises a first wavelength band and a second wavelength band that are modulated at a first frequency and a second frequency, respectively, and further comprising demodulating said first and second output signals, and wherein said demodulated first and second output signals are processed to provide said measurement.

18. The method of claim 14, and further comprising the step of differentiating the radiation incident on said first and second sides of said flat sheet product to eliminate cross talk.

19. The method of claim 18, wherein said step of differentiating comprises:
modulating the radiation incident on said first and second sides at different frequencies, and
demodulating said first and second reflection output signals, and said first and second transmissive output signals.

20. The method of claim 14, wherein said transmission gauge responds to radiation in a range selected from the group consisting of: infrared and microwave.

21. The method of claim 14, further comprising deriving from said measurement of degree of stratification of moisture a dry down calibration curve for said flat sheet product.

22. A measurement system for measuring a degree of stratification of moisture in a moving flat sheet product, said system comprising:
one or more sources that provides radiation incident to first and second sides of said moving flat sheet product at a measurement station adjacent said moving flat sheet product;
a first reflection gauge and a second reflection gauge that are located on said first and second sides of said moving flat sheet product at said measurement station and that respond to said radiation in the infrared range to provide first and second reflection output signals, respectively;
a first transmission gauge and a second transmission gauge that are located on said first and second sides of said moving flat sheet product at said measurement station and that provide first and second transmissive output signals, respectively; and
a controller that processes said first and second reflection output signals and said first and second transmissive output signals to provide a measurement of a degree of stratification of moisture within said moving flat sheet product, wherein said measurement comprises one or more of:
(a) a working ratio difference between a working ratio of said first transmission gauge and a working ratio of said first reflection gauge,
(b) a working ratio difference between a working ratio of said second transmission gauge and a working ratio of said second reflection gauge,
(c) a difference between a percent moisture of a bulk of said moving flat sheet product and a percent moisture of said first side or of said second side divided by an average percent moisture of an entire depth of said flat moving sheet product.

23. The measurement system of claim 22, wherein said degree of stratification comprises a measurement value of a location within a depth of said moving flat sheet product.

24. A method for measuring a degree of stratification of moisture in a moving flat sheet product, said method comprising:

providing radiation incident on first and second sides of said moving flat sheet product;

providing a first reflection output signal and a second reflection output signal derived from a reflection of said radiation incident on said first and second sides of said moving flat sheet product, wherein said first and second reflection is of said radiation in the infrared range;

providing a first transmissive output signal and a second transmissive output signal derived from an emergence of said radiation from said second and first sides of said moving flat sheet product, respectively, wherein said first and second reflection output signals are provided by first and second reflection gauges, respectively, and wherein said first and second transmissive output signals are provided by first and second transmission gauges, respectively; and processing said first and second reflection output signals and said first and second transmissive output signals to provide a measurement of a degree of stratification of moisture within said moving flat sheet product, wherein said measurement comprises one or more of:

(a) a working ratio difference between a working ratio of said first transmission gauge and a working ratio of said first reflection gauge, (b) a working ratio difference between a working ratio of said second transmission gauge and a working ratio of said second reflection gauge, and (c) a difference between a percent moisture of a bulk of said moving flat sheet product and a percent moisture of said first side or of said second side divided by an average percent moisture of an entire depth of said flat moving sheet product.

25. The method of claim 24, wherein said degree of stratification comprises a measurement value of a location within a depth of said moving flat sheet product.

* * * * *